(12) United States Patent  (10) Patent No.: US 8,382,828 B2
Roberts  (45) Date of Patent: *Feb. 26, 2013

(54) MITRAL ANNULOPLASTY RINGS (75) Inventor: Harold G. Roberts, Coral Springs, FL (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/975,830

(22) Filed: Dec. 22, 2010

(65) Prior Publication Data

US 2011/0093065 A1  Apr. 21, 2011

Related U.S. Application Data (63) Continuation of application No. 11/868,412, filed on Oct. 5, 2007, now Pat. No. 7,879,087.

(51) Int. Cl.
*A61F 2/24* (2006.01)
(52) U.S. Cl. ...................................................... 623/2.36
(58) Field of Classification Search ......... 623/2.36–2.42
See application file for complete search history.

(56) References Cited

U.S. PATENT DOCUMENTS

| | | |
|---|---|---|
| 3,656,185 A | 4/1972 | Carpentier |
| 4,042,979 A | 8/1977 | Angell |
| 4,055,861 A | 11/1977 | Carpentier et al. |
| 4,164,046 A | 8/1979 | Cooley |
| 4,217,665 A | 8/1980 | Bex et al. |
| 4,489,446 A | 12/1984 | Reed |
| 4,602,911 A | 7/1986 | Ahmadi et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A * | 4/1992 | Lam et al. ............ 623/2.36 |
| 5,201,880 A * | 4/1993 | Wright et al. ......... 623/2.37 |
| 5,258,021 A | 11/1993 | Duran |

(Continued)

FOREIGN PATENT DOCUMENTS

| | | |
|---|---|---|
| EP | 0338994 | 10/1989 |
| EP | 0595791 | 5/1994 |

(Continued)

OTHER PUBLICATIONS

Adams, David, et al., "Large Annuloplasty Rings Facilitate Mitral Valve Repair in Barlow's Disease," Society of Thoracic Surgeons 42$^{nd}$ Annual Meeting, Jan. 30-Feb. 1, 2006.

(Continued)

*Primary Examiner* — Alvin J. Stewart
(74) *Attorney, Agent, or Firm* — AnneMarie Kaiser; Guy Cumberbatch (57) ABSTRACT

A mitral annuloplasty ring with an inner core and an outer band located therearound. The ring has an anterior region, a posterior region opposite the anterior region, and two side regions therebetween. A cross-sectional width dimension of the outer band is greater in the posterior region of the ring than in the anterior region. A cross-sectional width dimension of a semi-flexible core is thinner in the anterior and posterior regions than in the side regions so that the mitral ring is more rigid in bending in the anterior-posterior direction. A tricuspid annuloplasty ring of the invention has an inner core and an outer band located therearound. The inner core has an anterior region separated across a gap from a septal region, and a posterior region. A cross-sectional width dimension of the outer band is greater in the septal region than either the anterior or posterior regions.

37 Claims, 4 Drawing Sheets

U.S. PATENT DOCUMENTS

| | | | |
|---|---|---|---|
| 5,306,296 A | 4/1994 | Wright et al. | |
| 5,376,112 A | 12/1994 | Duran | |
| 5,496,336 A | 3/1996 | Cosgrove et al. | |
| 5,593,435 A | 1/1997 | Carpentier et al. | |
| 5,607,471 A * | 3/1997 | Seguin et al. | 623/2.36 |
| 5,669,919 A | 9/1997 | Sanders et al. | |
| 5,674,279 A | 10/1997 | Wright et al. | |
| 5,674,280 A | 10/1997 | Davidson et al. | |
| 5,716,397 A * | 2/1998 | Myers | 623/2.36 |
| 5,776,189 A | 7/1998 | Khalid | |
| 5,824,066 A | 10/1998 | Gross | |
| 5,824,069 A | 10/1998 | Lemole | |
| 5,888,240 A | 3/1999 | Carpentier et al. | |
| 5,972,030 A | 10/1999 | Garrison et al. | |
| 6,019,739 A | 2/2000 | Rhee et al. | |
| 6,024,918 A | 2/2000 | Hendriks et al. | |
| 6,102,945 A * | 8/2000 | Campbell | 623/2.37 |
| 6,143,024 A * | 11/2000 | Campbell et al. | 623/2.36 |
| 6,159,240 A | 12/2000 | Sparer et al. | |
| 6,183,512 B1 | 2/2001 | Howanec, Jr. et al. | |
| 6,187,040 B1 * | 2/2001 | Wright | 623/2.36 |
| 6,217,610 B1 | 4/2001 | Carpentier et al. | |
| 6,231,602 B1 | 5/2001 | Carpentier et al. | |
| 6,250,308 B1 | 6/2001 | Cox | |
| 6,258,122 B1 | 7/2001 | Tweden et al. | |
| 6,332,893 B1 | 12/2001 | Mortier et al. | |
| 6,368,348 B1 * | 4/2002 | Gabbay | 623/2.36 |
| 6,391,054 B2 * | 5/2002 | Carpentier et al. | 623/2.37 |
| 6,406,493 B1 | 6/2002 | Tu et al. | |
| 6,416,548 B2 * | 7/2002 | Chinn et al. | 623/2.36 |
| 6,419,696 B1 | 7/2002 | Ortiz et al. | |
| 6,565,603 B2 | 5/2003 | Cox | |
| 6,602,288 B1 | 8/2003 | Cosgrove et al. | |
| 6,602,289 B1 * | 8/2003 | Colvin et al. | 623/2.37 |
| 6,619,291 B2 | 9/2003 | Hlavka et al. | |
| 6,709,456 B2 | 3/2004 | Langberg et al. | |
| 6,718,985 B2 | 4/2004 | Hlavka et al. | |
| 6,719,786 B2 | 4/2004 | Ryan et al. | |
| 6,726,717 B2 | 4/2004 | Alfieri et al. | |
| 6,730,121 B2 * | 5/2004 | Ortiz et al. | 623/2.17 |
| 6,749,630 B2 * | 6/2004 | McCarthy et al. | 623/2.36 |
| 6,764,510 B2 | 7/2004 | Vidlund et al. | |
| 6,786,924 B2 | 9/2004 | Ryan et al. | |
| 6,787,040 B2 | 9/2004 | Radunsky et al. | |
| 6,797,002 B2 | 9/2004 | Spence et al. | |
| 6,800,090 B2 | 10/2004 | Alferness et al. | |
| 6,802,860 B2 | 10/2004 | Cosgrove et al. | |
| 6,805,710 B2 * | 10/2004 | Bolling et al. | 623/2.36 |
| 6,805,711 B2 | 10/2004 | Quijano et al. | |
| 6,858,039 B2 * | 2/2005 | McCarthy | 623/2.36 |
| 6,908,482 B2 | 6/2005 | McCarthy et al. | |
| 6,918,917 B1 | 7/2005 | Nguyen et al. | |
| 6,921,407 B2 | 7/2005 | Nguyen et al. | |
| 6,942,694 B2 | 9/2005 | Liddicoat et al. | |
| 6,955,689 B2 | 10/2005 | Ryan et al. | |
| 6,966,924 B2 | 11/2005 | Holmberg | |
| 6,986,775 B2 | 1/2006 | Morales et al. | |
| 7,101,395 B2 | 9/2006 | Tremulis et al. | |
| 7,118,595 B2 | 10/2006 | Ryan et al. | |
| 7,125,421 B2 | 10/2006 | Tremulis et al. | |
| 7,166,126 B2 | 1/2007 | Spence et al. | |
| 7,166,127 B2 | 1/2007 | Spence et al. | |
| 7,220,277 B2 | 5/2007 | Arru et al. | |
| 7,276,079 B2 | 10/2007 | Sievers | |
| 7,294,148 B2 * | 11/2007 | McCarthy | 623/2.36 |
| 7,329,280 B2 * | 2/2008 | Bolling et al. | 623/2.36 |
| 7,367,991 B2 * | 5/2008 | McCarthy et al. | 623/2.36 |
| 7,371,259 B2 * | 5/2008 | Ryan et al. | 623/2.36 |
| 7,374,572 B2 | 5/2008 | Gabbay | |
| 7,377,940 B2 | 5/2008 | Ryan et al. | |
| 7,396,364 B2 | 7/2008 | Moaddeb et al. | |
| 7,427,291 B2 | 9/2008 | Liddicoat et al. | |
| 7,452,376 B2 * | 11/2008 | Lim et al. | 623/2.36 |
| 7,510,577 B2 | 3/2009 | Moaddeb et al. | |
| 7,575,595 B2 | 8/2009 | Ingle et al. | |
| 7,608,102 B2 | 10/2009 | Adams et al. | |
| 7,608,103 B2 * | 10/2009 | McCarthy | 623/2.36 |
| 7,674,286 B2 | 3/2010 | Alfieri et al. | |
| 7,879,087 B2 * | 2/2011 | Roberts | 623/2.36 |
| 7,959,673 B2 * | 6/2011 | Carpentier et al. | 623/2.36 |
| D642,684 S * | 8/2011 | Drake | D24/155 |
| 7,993,395 B2 * | 8/2011 | Vanermen et al. | 623/2.36 |
| 8,142,495 B2 * | 3/2012 | Hasenkam et al. | 623/2.37 |
| 8,142,496 B2 * | 3/2012 | Berreklouw | 623/2.37 |
| 8,152,844 B2 * | 4/2012 | Rao et al. | 623/2.36 |
| 8,163,012 B2 * | 4/2012 | Fawzy et al. | 623/2.36 |
| 2001/0010018 A1 * | 7/2001 | Cosgrove et al. | 623/2.11 |
| 2001/0021874 A1 * | 9/2001 | Carpentier et al. | 623/2.37 |
| 2001/0049557 A1 * | 12/2001 | Chinn et al. | 623/2.36 |
| 2002/0133180 A1 * | 9/2002 | Ryan et al. | 606/148 |
| 2002/0198595 A1 * | 12/2002 | Brendzel et al. | 623/2.39 |
| 2003/0033009 A1 | 2/2003 | Gabbay | |
| 2003/0040793 A1 * | 2/2003 | Marquez | 623/2.36 |
| 2003/0050693 A1 * | 3/2003 | Quijano et al. | 623/2.11 |
| 2003/0078654 A1 * | 4/2003 | Taylor et al. | 623/2.36 |
| 2003/0083742 A1 * | 5/2003 | Spence et al. | 623/2.16 |
| 2003/0176917 A1 * | 9/2003 | Ryan et al. | 623/2.11 |
| 2003/0199975 A1 * | 10/2003 | Gabbay | 623/2.36 |
| 2004/0044406 A1 * | 3/2004 | Woolfson et al. | 623/2.11 |
| 2004/0078074 A1 * | 4/2004 | Anderson et al. | 623/2.11 |
| 2004/0176839 A1 * | 9/2004 | Huynh et al. | 623/2.4 |
| 2004/0249452 A1 | 12/2004 | Adams et al. | |
| 2004/0249453 A1 * | 12/2004 | Cartledge et al. | 623/2.37 |
| 2005/0004665 A1 * | 1/2005 | Aklog | 623/2.36 |
| 2005/0004669 A1 * | 1/2005 | Sievers | 623/2.36 |
| 2005/0038509 A1 * | 2/2005 | Ashe | 623/2.36 |
| 2005/0043791 A1 * | 2/2005 | McCarthy et al. | 623/2.36 |
| 2005/0060030 A1 * | 3/2005 | Lashinski et al. | 623/2.37 |
| 2005/0065598 A1 * | 3/2005 | Mathis et al. | 623/2.11 |
| 2005/0119734 A1 * | 6/2005 | Spence et al. | 623/2.11 |
| 2005/0125011 A1 * | 6/2005 | Spence et al. | 606/144 |
| 2005/0131533 A1 * | 6/2005 | Alfieri et al. | 623/2.36 |
| 2005/0165479 A1 * | 7/2005 | Drews et al. | 623/2.38 |
| 2005/0182487 A1 * | 8/2005 | McCarthy et al. | 623/2.11 |
| 2005/0192666 A1 * | 9/2005 | McCarthy | 623/2.36 |
| 2005/0228496 A1 * | 10/2005 | Mensah et al. | 623/2.41 |
| 2005/0256567 A1 * | 11/2005 | Lim et al. | 623/2.36 |
| 2005/0256568 A1 * | 11/2005 | Lim et al. | 623/2.36 |
| 2005/0256569 A1 * | 11/2005 | Lim et al. | 623/2.36 |
| 2005/0267572 A1 | 12/2005 | Schoon et al. | |
| 2005/0278022 A1 | 12/2005 | Lim | |
| 2005/0288781 A1 * | 12/2005 | Moaddeb et al. | 623/2.37 |
| 2006/0015178 A1 | 1/2006 | Moaddeb et al. | |
| 2006/0015179 A1 | 1/2006 | Bulman-Fleming et al. | |
| 2006/0020336 A1 | 1/2006 | Liddicoat | |
| 2006/0025858 A1 | 2/2006 | Alameddine | |
| 2006/0030885 A1 | 2/2006 | Hyde | |
| 2006/0069430 A9 * | 3/2006 | Rahdert et al. | 623/2.36 |
| 2006/0100697 A1 * | 5/2006 | Casanova | 623/2.11 |
| 2006/0129236 A1 * | 6/2006 | McCarthy | 623/2.36 |
| 2006/0136053 A1 * | 6/2006 | Rourke et al. | 623/2.36 |
| 2006/0184240 A1 * | 8/2006 | Jimenez et al. | 623/2.36 |
| 2006/0184241 A1 * | 8/2006 | Marquez | 623/2.36 |
| 2006/0190077 A1 * | 8/2006 | Ryan et al. | 623/2.11 |
| 2006/0229708 A1 * | 10/2006 | Powell et al. | 623/1.24 |
| 2007/0038296 A1 * | 2/2007 | Navia et al. | 623/2.36 |
| 2007/0100441 A1 * | 5/2007 | Kron et al. | 623/2.36 |
| 2007/0156234 A1 * | 7/2007 | Adzich et al. | 623/2.11 |
| 2007/0162111 A1 | 7/2007 | Fukamachi et al. | |
| 2007/0162112 A1 * | 7/2007 | Burriesci et al. | 623/2.36 |
| 2007/0173931 A1 * | 7/2007 | Tremulis et al. | 623/2.11 |
| 2007/0191940 A1 * | 8/2007 | Arru et al. | 623/2.37 |
| 2007/0299513 A1 * | 12/2007 | Ryan et al. | 623/2.36 |
| 2008/0058924 A1 * | 3/2008 | Ingle et al. | 623/2.36 |
| 2008/0086203 A1 * | 4/2008 | Roberts | 623/2.36 |
| 2008/0091059 A1 * | 4/2008 | Machold et al. | 600/37 |
| 2009/0036979 A1 * | 2/2009 | Redmond et al. | 623/2.36 |
| 2009/0132036 A1 * | 5/2009 | Navia | 623/2.36 |
| 2009/0157176 A1 * | 6/2009 | Carpentier et al. | 623/2.36 |
| 2009/0177276 A1 * | 7/2009 | Carpentier et al. | 623/2.36 |
| 2009/0177278 A1 * | 7/2009 | Spence | 623/2.37 |
| 2009/0192602 A1 | 7/2009 | Kuehn | |
| 2009/0192603 A1 | 7/2009 | Ryan | |
| 2009/0192604 A1 | 7/2009 | Gloss | |
| 2009/0192606 A1 | 7/2009 | Gloss et al. | |
| 2009/0264996 A1 * | 10/2009 | Vanermen et al. | 623/2.36 |
| 2009/0276038 A1 * | 11/2009 | Tremulis et al. | 623/2.11 |

| | | | | |
|---|---|---|---|---|
| 2009/0287303 | A1* | 11/2009 | Carpentier | 623/2.36 |
| 2010/0076549 | A1* | 3/2010 | Keidar et al. | 623/2.36 |
| 2010/0076551 | A1* | 3/2010 | Drake | 623/2.36 |
| 2010/0145440 | A1* | 6/2010 | Keranen | 623/2.37 |
| 2010/0152844 | A1* | 6/2010 | Couetil | 623/2.36 |
| 2010/0168845 | A1* | 7/2010 | Wright | 623/2.36 |
| 2010/0174365 | A1* | 7/2010 | Parravicini et al. | 623/2.36 |

FOREIGN PATENT DOCUMENTS

| | | |
|---|---|---|
| EP | 0860151 | 8/1998 |
| EP | 1034753 | 9/2000 |
| FR | 2708458 | 8/1993 |
| WO | WO 95/03757 | 2/1995 |
| WO | WO 01/19292 | 3/2001 |
| WO | WO 01/26586 | 4/2001 |
| WO | WO 01/47438 | 7/2001 |
| WO | WO 01/87191 | 11/2001 |
| WO | WO 02/03892 | 1/2002 |
| WO | WO 03/020178 | 3/2003 |
| WO | WO 03/041617 | 5/2003 |
| WO | WO 2004/004607 | 1/2004 |
| WO | WO 2005/034813 | 4/2005 |
| WO | WO 2005/110290 | 11/2005 |
| WO | WO 2007/050506 | 5/2007 |

OTHER PUBLICATIONS

Alonso-Lei, M.D., et al., Adjustable Annuloplasty for Tricuspid Insufficiency, The annals of Thoracic Surgery, vol. 46, No. 3, pp. 368-369, Sep. 1988.

Bolling, Mitral Valve Reconstruction in the Patient With Heart Failure, Heart Failure Reviews, 6, pp. 177-185, 2001.

Bolling, et al., Surgical Alternatives for Heart Failure, The Journal of Heart and Lung Transplantation, vol. 20, No. 7, pp. 729-733, 2001.

Carpentier, et al. "The 'Physio-Ring': An Advanced Concept in Mitral Valve Annuloplasty," Society of Thoracic Surgeons 31st Annual meeting, Jan. 30-Feb. 2, 1995.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

Carpentier, et al., *Reconstructive Valve Surgery*, Chapter 19—Reconstructive Techniques, ISBN No. 978-0-7216-9168-8, Sanders Elsevier Publishing, Maryland Heights, Missouri, 2010.

Cochran, et al. Effect of Papillary Muscle Position on Mitral Valve Function: Relationship to Homografts, The Society of Thoracic Surgeons, pp. 5155-5161, 1998.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Miller, D. Craig, M.D., "Ischemic Mitral Regurgitation Redux—To Repair or Replace?", The Journal of Thoracic & Cardiovascular Surgery, Dec. 2001, vol. 122, No. 6, pp. 1059-1062.

Salgo, et al., Effect of Annular Shape on Leaflet Curvature in Reducing Mitral Leaflet, American Heart Association, Circulation 200; pp. 106-711.

Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000.

Techniques for 3D Quantitative Echocardiography, University of Washington Cardiovascular Research & Training Center Cardiac Imaging Research Lab, pp. 1-5, Oct. 2003.

Watanabe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association © 2005; ISSN: 1524-4539.

Salgo, et al., Effect of Annular Shape on Leaflet Curvature in Reducing Mitral Leaflet Stress. American Heart Association, Circulation 2002; 106:711, 16 pages.

* cited by examiner

MITRAL ANNULOPLASTY RINGS

RELATED APPLICATION(S)

The present application is a continuation of U.S. patent application Ser. No. 11/868,412, filed Oct. 5, 2007, which claims priority under 35 U.S.C. §119(e) to U.S. Provisional Application No. 60/828,458, filed Oct. 6, 2006.

FIELD OF THE INVENTION

The present invention relates to prosthetic annuloplasty rings for effecting and maintaining a mitral or tricuspid repair.

BACKGROUND OF THE INVENTION

Repair of the mitral and tricuspid valves is a steadily growing and vital part of cardiac surgery. Experience has shown that effecting and maintaining a mitral or tricuspid repair requires a prosthetic annuloplasty ring. A major goal of a ring is to restore the shape of the annulus to its normal geometry. In mitral regurgitation, the annulus often becomes circular. The ring should restore the normal "D" shape. Fully flexible rings or bands do nothing to correct the shape of the pathologic mitral annulus. Only rigid or semi-flexible rings mold the shape of the mitral annulus.

One of the most common causes of a failed valve repair is dehiscence of the ring from the annulus. For the mitral annulus, dehiscence almost invariably occurs along the posterior portion of the ring, since this is the area of the annulus where size reduction and increased stress occurs.

SUMMARY OF THE INVENTION

Briefly, and in accordance with the foregoing, embodiments of the present invention provide prosthetic annuloplasty rings which are configured to minimize the likelihood of dehiscence while maintaining the shape of a healthy valve annulus.

In one embodiment, the present invention provides a saddle-shaped annuloplasty ring with a 4:3 ratio between the transverse dimension and vertical dimension for repairing the mitral valve. The ring is shaped and configured such that it closely mimics the geometry of a healthy mitral annulus. Preferably, the ring includes trigone markings to aid the surgeon with regard to correct positioning. The ring includes a core, an outer band and a cover. The core may be formed of titanium which provides that the ring is rigid. Alternatively, the core may be formed of a more flexible metal, such as Elgiloy or Nitinol, which would provide that the ring is semi-flexible, in which case preferably the ring is provided as being 20% more rigid in the vertical compared to the transverse dimension.

Preferably, the outer band comprises silicon rubber, and the cover comprises polyester cloth. Additionally, the width of the outer band is desirably greater in the posterior region of the ring than at the anterior region. This facilitates the placement of overlapping sutures at the posterior annulus to provide extra security against ring dehiscence.

Also disclosed is a tricuspid ring which is configured to minimize the likelihood of dehiscence while maintaining the shape of a healthy valve annulus. The ring is not complete in the 10% of the circumference around the anteroseptal commissure. This prevents suture injury to the conduction system. The ring may have a somewhat spiral shape that mimics the shape of the healthy tricuspid annulus, and the posterior half of the posterior annulus as well as the septal annulus slope down, preferably by about 4 mm. The ring includes a core which is formed of a semi-flexible material, such as Elgiloy or Nitinol, thereby providing that the ring is semi-flexible rather than rigid, which should decrease the odds of dehiscence. The width of an outer band of the ring is greatest in the septal region, thereby allowing overlapping sutures at the septal annulus to allow better anchoring of the ring.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The organization and manner of the structure and operation of the invention, together with further objects and advantages thereof, may best be understood by reference to the following description taken in connection with the accompanying drawings wherein like reference numerals identify like elements in which:

FIGS. 1', 2', 3A', 3B', 3C', 4A', 4B' and 4C' correspond to FIGS. 1, 2, 3A, 3B, 3C, 4A, 4B, and 4C, respectively, but show preferred dimensions in millimeters;

FIGS. 7A', 7B', 8A', and 8B' correspond to FIGS. 7A, 7B, 8A and 8B, respectively, but show preferred dimensions in millimeters.

DETAILED DESCRIPTION OF THE PREFERRED EMBODIMENTS

While this invention may be susceptible to embodiment in different forms, there are shown in the drawings and will be described herein in detail, specific embodiments with the understanding that the present disclosure is to be considered an exemplification of the principles of the invention, and is not intended to limit the invention to that as illustrated.

Figures 1, 2:
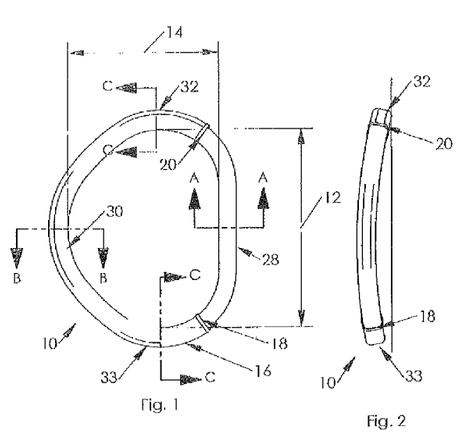
FIG. 1 is a top plan view of a mitral annuloplasty ring which is in accordance with an embodiment of the present invention.
FIG. 2 is a side view of the annuloplasty ring shown in FIG. 1.

FIG. 1 is a top plan view of a mitral annuloplasty ring 10 which is in accordance with an embodiment of the present invention, while FIG. 2 is a side view. The ring 10 is configured to minimize the likelihood of dehiscence while maintaining the shape of a healthy valve annulus. The ring 10 is a saddle-shaped ring (described below) with a 4:3 ratio between a transverse dimension (identified with reference numeral 12 in FIG. 1) and vertical dimension (identified with reference numeral 14 in FIG. 1). The reader will note that the vertical dimension is as viewed in plan view with an anterior side 28 up, though it is not oriented in this way in the drawings. The ring 10 is shaped and configured such that it closely mimics the geometry of a healthy mitral annulus. Preferably, an exterior surface 16 of the ring 10 includes trigone markings 18, 20 to aid the surgeon with regard to correct positioning. The trigone markings 18, 20 are located at the junction of the anterior region 28 and the side regions 32, 33. Preferably, the range of ring sizes varies from a transverse internal diameter of 24-36 mm. The size needed is determined by measuring the area of the anterior leaflet with templates corresponding to the various ring sizes.

Figure 3A:
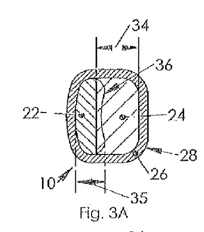
FIGS. 3A, 3B and 3C are cross-sectional views of the annuloplasty ring shown in FIG. 1, taken along lines A-A, B-B and C-C, respectively, where a core of the ring is a formed metal ring.
Figure 3B:
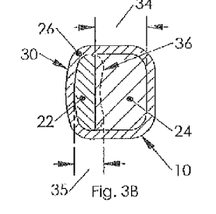
Figure 3C:
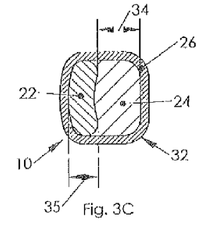

FIGS. 3A, 3B and 3C are cross-sectional views of the ring 10 taken along lines A-A, B-B and C-C, respectively, of FIG. 1. As shown, the ring 10 consists of a core 22, an outer band 24 and a cover 26.

In a first embodiment of the present invention, the core 22 is formed of titanium which provides that the ring 10 is rigid. Alternatively, the core 22 may be formed of a more flexible metal which would provide that the ring 10 is semi-flexible rather than rigid. In this sense, the term "semi-flexible" refers to annuloplasty ring materials that are somewhat rigid but do flex due to the natural forces after implant. Semi-flexible means not as rigid as titanium, but more rigid than "fully flexible" rings made of, for example, silicone. Specifically, in a second embodiment of the present invention the core 22 is made of Elgiloy, and in a third embodiment of the present invention the core 22 is made of Nitinol. Regardless of what the core 22 is comprised, preferably the outer band 24 comprises silicon rubber, and the cover 26 comprises polyester cloth. Although not specifically shown, the ring 10 may also include a barium impregnated string to render the ring radiopaque.

FIG. 3A provides a cross-sectional view of an anterior region 28 of the ring 10, while FIG. 3B provides a cross-sectional view of a posterior region 30, and FIG. 3C provides a cross-sectional view of side regions 32 and 33, which are identical in cross-section. In a "saddle-shaped" ring, the ring periphery describes a three-dimensional path that gradually curves up at the anterior and posterior regions 28, 30, and down at the side regions 32 and 33, as seen in FIGS. 2 and 2'. In the illustrated embodiment, the anterior and posterior regions 28, 30 rise to about the same height, though they may be at different heights as desired.

As identified by comparing FIG. 3A to FIG. 3B, the width (dimension 34 in FIGS. 3A, 3B and 3C) of the outer band 24 is greater, such as 30% greater, in the posterior region 30 of the ring 10 than at the anterior region 28. This facilitates the placement of overlapping sutures at the posterior annulus to provide extra security against ring dehiscence. Preferably, the width 34 of the band 24 begins to change at the trigone markings 18, 20 on the ring 10, gradually becoming thicker until a maximum at the mid-point of the posterior region 30. It should also be noted that the width of the outer band 24 at the posterior region 30 is equal to or greater than the width of the band at both the side regions 32, 33. For example, as seen by comparing FIGS. 3B' and 3C', and 4B' and 4C', the width of the outer band 24 at the posterior region 30 ranges between 1.3 mm (with a titanium core 22) to 2.2 mm (with a semi-flexible core), while the width of the outer band 24 at the side regions is a maximum of 1.3 mm (same with all core materials). In contrast, depending on what form and material of the inner core 22, the width of the outer band 24 at the anterior region 28 is less than, equal to, or greater than the width at the side regions 32, 33, as seen by comparing FIGS. 3A' and 3C', and 4A' and 4C'.

As discussed above, the core 22 can be provided as being formed of titanium which would provide that the ring 10 is rigid. Alternatively, the core 22 may be formed of a more flexible metal, such as Elgiloy or Nitinol, which would provide that the ring is semi-flexible rather than rigid. This semi-flexible alloy allows the ring 10 to flex during the cardiac cycle without losing its shape. Hopefully, the flexibility will minimize local annular stresses likely to produce dehiscence.

If Elgiloy or Nitinol is used for the core 22, the core 22 may be shaped somewhat differently than if titanium is used. This change in cross-sectional shape is identified in FIGS. 3A, 3B, 4A, 4B, 3A', 3B', 4A' and 4B' using a dotted line 36. The dotted line 36 represents the outer surface of a titanium core 22, in contrast to the solid cross-section of a semi-flexible (e.g., Nitinol or Elgiloy) core. In the illustrated embodiment, the solid cross-section includes an axially-oriented surface that defines the outer surface of a semi-flexible core 22, in contrast to the dotted line 36 which represents the outer surface of a titanium core and has a concave outer profile in radial section as shown.

If Elgiloy or Nitinol is used for the core 22, the ring 10 is preferably configured such that it is 20% more rigid in the vertical dimension 14 (the anterior-posterior direction) as compared to the transverse dimension 12. In other words, it is harder to squeeze the ring 10 between the anterior and posterior regions 28, 30 in FIG. 1 than it is to squeeze the ring 10 between the side regions 32, 33. This difference in rigidity/flexibility derives from a particular cross-sectional shape of the core 22 which overcomes the natural inclination for the ring to be more flexible in the vertical dimension. That is, if the ring 10 were the same cross section all the way around its periphery, the longer moment arm in bending when squeezing the anterior and posterior regions 28, 30 would naturally permit greater flexing or inward movement than when squeezing the side regions.

In an exemplary embodiment, the width (dimension 35 in FIGS. 3A-3C and 4A-4C) of the core 22 may be thinner in the anterior and posterior regions (28 and 30) than in side regions 32 and 33. More specifically, the width dimension 35 is shown measuring the extent of the core 22 as seen in dotted line 36, but the width for cores of semi-flexible material such as Elgiloy or Nitinol would only extend to the solid line cross-section. There is thus a difference in the width dimension at the anterior and posterior regions for rings made of a semi-flexible material versus a ring made of a rigid material, such as titanium. However, the core width 35 of both semi-flexible and rigid rings remains the same at the side regions 32, 33 because it is desirable to maintain in semi-flexible rings the resistance to bending from squeezing the ring 10 in the transverse dimension (vertical in FIG. 1).

Preferably, the width 35 of the core 22 begins to change at the trigone markings 18, 20 on the ring 10, and most preferably reduces gradually from the trigones to the mid-point of the anterior and posterior regions 28, 30. In particular, the cross-section of the core 22 of semi-flexible rings desirably attains a maximum at the side regions 32, 33, as seen in FIGS. 3C and 4C, and gradually reduces toward the anterior and posterior regions 28, 30, as seen in solid line in FIGS. 3A-3B and 4A-4B. Alternatively, an abrupt change in cross-section or one which while not abrupt is sharp or non-linear may be utilized. For instance, from a maximum at the side regions 32, 33, the width 35 may decrease smoothly but rapidly over an arc of, say, 10° to the lesser width of the anterior and posterior regions 28, 30. It is also worth mentioning that the reduced width 35 at the anterior and posterior regions 28, 30 may be equal or not as desired.

If Nitinol is used as the core 22 of the ring 10, the ring 10 could be used in association with a method which is in accordance with an embodiment of the present invention. Specifically, the design would be uniquely well suited for minimally invasive valve cases with working ports too small to accommodate currently available rigid rings. At present, only fully flexible prostheses, such as the Duran ring or the Cosgrove band, can traverse these 20 mm working ports. These fully flexible prostheses do nothing to decrease the vertical dimension, which has been increasingly recognized as important in maintaining a durable valve repair. By immersing the Nitinol core ring in iced saline, the ring would be readily deformable (martensite phase). This would facilitate passage of the ring through 20 mm working ports used in robotic valve repair. As the ring warmed up in the chest, it would resume its saddle shape (austenite phase). The silicon rubber band would facilitate anchoring the band to the annulus with Coalescent Nitinol clips. Until now, these clips could only be used with fully flexible prostheses.

Figure 4A:
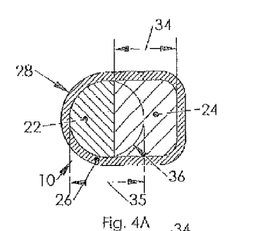
FIGS. 4A, 4B and 4C are cross-sectional views of the annuloplasty ring shown in FIG. 1, taken along lines A-A, B-B and C-C, respectively, where a core of the ring is a round wire.
Figure 4B:
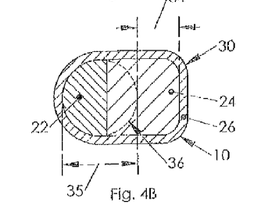
Figure 4C:
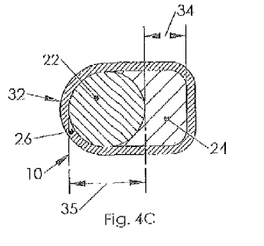

Regardless of whether the core 22 is made of titanium, Elgiloy or Nitinol, the core 22 can be formed of a round wire, in which case the cross-sectional views taken along lines A-A, B-B and C-C of FIG. 1 would appear as shown FIGS. 4A, 4B and 4C, respectively. Alternatively, the core 22 can be a formed metal ring, in which case the cross-sectional views taken along lines A-A, B-B and C-C of FIG. 1 would appear as shown FIGS. 3A, 3B and 3C, respectively. A dotted line 36 is also used in FIGS. 3B and 4B to show the situation where the core 22 is an Elgiloy or Nitinol formed metal ring.

As shown in FIG. 2, the ring 10 may be provided as being slightly asymmetric, with the portion at the left trigone 20 one mm deeper than the right trigone 18. In other words, the side regions 32, 33 drop to different heights, with the left side 32 (as viewed from above with the anterior side 28 up) lying on a reference line see in FIG. 2 while the right side 33 is slightly spaced therefrom. This more closely reproduces the true natural shape of the healthy mitral annulus. Even if the ring 10 is provided as being slightly asymmetric, the core 22 can be titanium, Elgiloy, or Nitinol, for example.

FIGS. 1', 2', 3A', 3B', 3C', 4A', 4B' and 4C' correspond to FIGS. 1, 2, 3A, 3B, 3C, 4A, 4B and 4C, respectively, but show preferred dimensions, in millimeters. It should be noted that the dimensions shown are only one example, intended to provide the desired properties described herein, and other dimensions may be used while staying fully within the scope of the present invention. For instance, the magnitudes shown may represent dimensionless ratios of the various dimensions. In one example, as seen in FIG. 2', the left side 32 (see FIG. 2) has a height of 5 mm from the summit of the anterior side 28, while the right side 33 has an equivalent height of 4 mm. The downward drop of the left side 32 may be more or less, but desirably is about 20% more than downward drop of the right side 33.

Figure 5:
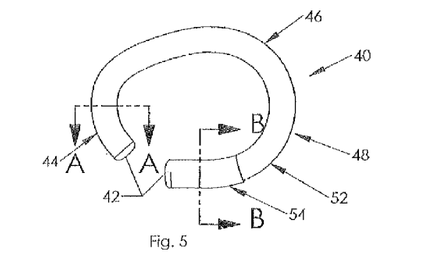
FIG. 5 is a top plan view of a tricuspid annuloplasty ring which is in accordance with an embodiment of the present invention.
Figure 6:
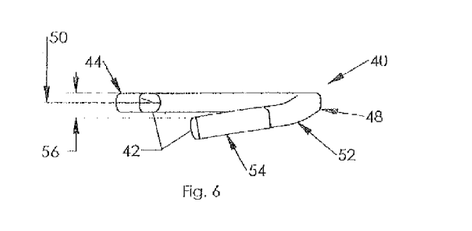
FIG. 6 is a side view of the annuloplasty ring shown in FIG. 5.

FIG. 5 is a top plan view of a tricuspid ring 40 which is in accordance with an embodiment of the present invention, while FIG. 6 is a side view. The ring 40 is configured to minimize the likelihood of dehiscence while maintaining the shape of a healthy valve annulus. Preferably, the ring 40 comes in different sizes with an internal diameter being between 24-36 mm. Regardless of the size, the ring 40 is not complete in the 10% of the circumference around the anteroseptal commissure (i.e., area 42 in FIGS. 6 and 7). This prevents suture injury to the conduction system. The ring 40 has a somewhat spiral shape that mimics the shape of the healthy tricuspid annulus. The anterior annulus 44 and anterior half 46 of the posterior annulus 48 are in the same plane (identified with line 50 in FIG. 7). The posterior half 52 of the posterior annulus 48 as well as the septal annulus 54 slope down, preferably 4 mm (identified with dimension 56 in FIG. 7).

Figure 7A:
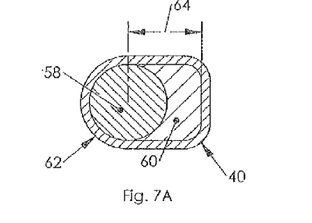
FIGS. 7A and 7B are cross-sectional views of the annuloplasty ring shown in FIG. 5, taken along lines A-A and B-B, respectively, where a core of the ring is a round wire.
Figure 7B:
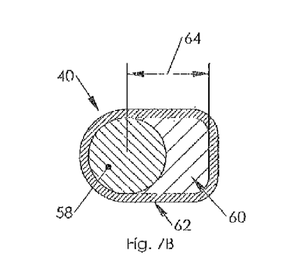

FIGS. 7A and 7B are cross-sectional views of the ring 40 taken along lines A-A and B-B, respectively, of FIG. 5. As shown, like the ring 20 described hereinabove, the ring 40 includes a core 58, an outer band 60 and a cover 62. Preferably, the core 58 is formed of a semi-flexible material. Specifically, in one embodiment, the core 58 is provided as being formed of Elgiloy. In another embodiment, the core is provided as being formed of Nitinol. Regardless, using a semi-flexible material for the core 58 provides that the ring 40 is semi-flexible rather than rigid, which should decrease the odds of dehiscence. Currently, only rigid rings have been specifically constructed for tricuspid repair. Regardless of what the core 58 is comprised, preferably the outer band 60 is formed of a SILASTIC material, such as silicone, and the cover 62 is comprised of polyester cloth.

FIG. 7A is a cross-sectional view taken along line A-A of FIG. 5 and provides a cross-sectional view of the anterior region of the ring 40. This view also applies to the posterior region. In contrast, FIG. 7B provides a cross-sectional view taken along line B-B of FIG. 5 and corresponds to the septal region of the ring. As recognized by comparing FIG. 7A to FIG. 7B, the width (dimension 64 in FIGS. 7A and 7B) of the outer band 60 is greater (such as 1.3 times greater) in the septal region 54 than either the anterior region 44 or posterior region 48. This allows overlapping sutures at the septal annulus 54 to allow better anchoring of the ring 40.

As discussed above, an embodiment of the present invention provides that the core 58 of the ring 40 is provided as being formed of Nitinol. This allows further flexibility and further minimizes the likelihood of dehiscence. If Nitinol is used as the core 58 of the ring 40, the ring 40 could be used in association with a method which is in accordance with an embodiment of the present invention. Specifically, cooling the ring 40 in iced saline will facilitate passage of the ring 40 through small working ports for minimal access valve surgery. Additionally, the diameter 64 of the silicone rubber band 60 will facilitate attachment of the ring 40 to the annulus with Coalescent Nitinol clips.

Figure 8A:
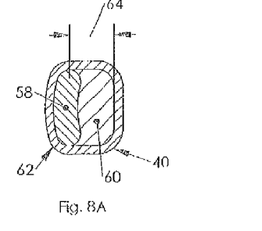
FIGS. 8A and 8B are cross-sectional views of the annuloplasty ring shown in FIG. 5, taken along lines A-A and B-B, respectively, where a core of the ring is a formed metal ring.
Figure 8B:
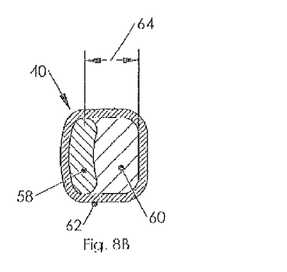

Regardless of whether the core 58 is made of Elgiloy or Nitinol, the core 58 can be formed of a round wire, in which case the cross-sectional views taken along lines A-A and B-B of FIG. 5 would appear as shown FIGS. 7A and 7B, respectively. Alternatively, the core 58 can be a formed metal ring, in which case the cross-sectional views taken along lines A-A and B-B of FIG. 5 would appear as shown FIGS. 8A and 8B, respectively.

FIGS. 7A', 7B', 8A', and 8B' correspond to FIGS. 7A, 7B, 8A, and 8B, respectively, but show preferred dimensions in millimeters. It should be noted that the dimensions shown are only one example, intended to provide the desired properties described herein, and other dimensions may be used while staying fully within the scope of the present invention. For instance, the magnitudes shown may represent dimensionless ratios of the various dimensions.

Disclosed herein are several embodiments of mitral and tricuspid rings, each of which is configured to minimize the likelihood of dehiscence while maintaining the shape of a healthy valve annulus. While preferred embodiments of the invention are shown and described, it is envisioned that those skilled in the art may devise various modifications without departing from the spirit and scope of the foregoing description.

What is claimed is:

1. A mitral annuloplasty ring, comprising:
   an inner core and an outer band located around the outside of the inner core for anchoring the ring to a mitral annulus;
   the ring having an anterior region and a posterior region opposite the anterior region, and two side regions between the anterior and posterior regions, the ring having a vertical dimension extending between the anterior region and posterior region and a transverse dimension extending between the side regions, wherein the transverse dimension is greater than the vertical dimension;
   wherein the ring is saddle-shaped and describes a three-dimensional path that gradually curves up at the anterior and posterior regions and down at the side regions, and wherein the ring is asymmetric with the two side regions curving down to different heights; and
   wherein the anterior and posterior regions rise to different heights.

2. The mitral annuloplasty ring of claim 1, wherein a width dimension of the outer band as seen in cross-section through the ring is greater in the posterior region of the ring than in the anterior region.

3. The mitral annuloplasty ring of claim 2, wherein the width dimension of the outer band is 30% greater in the posterior region of the ring than in the anterior region.

4. The mitral annuloplasty ring of claim 1, wherein the inner core is made of ELGILOY alloy.

5. The mitral annuloplasty ring of claim 1, wherein a width dimension of the core as seen in cross-section through the ring is thinner in the anterior and posterior regions than in the side regions.

6. The mitral annuloplasty ring of claim 5, wherein the radial width of the core has a maximum at the side regions that is greater than both the anterior and posterior regions.

7. The mitral annuloplasty ring of claim 1, wherein the core is a round metallic wire.

8. The mitral annuloplasty ring of claim 1, wherein the core is a formed metal ring having a concave outer surface.

9. The mitral annuloplasty ring of claim 1, wherein the core is metal ring and has an axially-oriented outer surface.

10. A mitral annuloplasty ring, comprising:
    a semi-flexible metallic inner core having an anterior region and a posterior region opposite the anterior region, and two side regions between the anterior and posterior regions, and wherein trigones are defined at the junction between the anterior region and the two side regions, the ring having a vertical dimension extending between the anterior region and posterior region and a larger transverse dimension extending between the side regions, and wherein the radial width of the core has a maximum at the side regions that is greater than both the anterior and posterior regions, wherein there is an abrupt change in cross-section in the radial width of the core between the side regions and at least one of the anterior and posterior regions; and
    an outer band located around the outside of the inner core for anchoring the ring to a mitral annulus.

11. The mitral annuloplasty ring of claim 10, wherein the abrupt change in cross-section in the radial width of the core extends over an arc around the core of about 10°.

12. The mitral annuloplasty ring of claim 10, wherein the radial width of the core at the anterior region is not equal to the radial width of the core at the posterior region.

13. The mitral annuloplasty ring of claim 10, wherein the core is a metal ring and has an axially-oriented outer surface at at least one of the anterior and posterior regions.

14. The mitral annuloplasty ring of claim 10, wherein the difference in width dimension of the core in the anterior and posterior regions relative to the side regions is such that the core is 20% more rigid in the vertical dimension as compared to the transverse dimension.

15. The mitral annuloplasty ring of claim 10, wherein a width dimension of the outer band as seen in cross-section through the ring is greater in the posterior region of the ring than in the anterior region.

16. The mitral annuloplasty ring of claim 10, wherein the anterior and posterior regions rise to different heights.

17. The mitral annuloplasty ring of claim 10, wherein the core is a round metallic wire.

18. The mitral annuloplasty ring of claim 10, wherein the core is a formed metal ring having a concave outer surface.

19. The mitral annuloplasty ring of claim 10, wherein the core is metal ring and has an axially-oriented outer surface.

20. A mitral annuloplasty ring, comprising:
    an inner core and an outer band located around the outside of the inner core for anchoring the ring to a mitral annulus;
    the ring having an anterior region and a posterior region opposite the anterior region, and two side regions between the anterior and posterior regions, the ring having a vertical dimension extending between the anterior region and posterior region and a transverse dimension extending between the side regions, wherein the transverse dimension is greater than the vertical dimension;
    wherein the ring is saddle-shaped and describes a three-dimensional path that gradually curves up at the anterior and posterior regions and down at the side regions, and wherein the ring is asymmetric with the two side regions curving down to different heights; and
    wherein a width dimension of the outer band as seen in cross-section through the ring is greater in the posterior region of the ring than in the anterior region.

21. The mitral annuloplasty ring of claim 20, wherein the width dimension of the outer band changes gradually from trigone markings, located at junctions of the anterior region and the side regions, to a maximum at a mid-point of the posterior region.

22. The mitral annuloplasty ring of claim 20, wherein a width dimension of the core as seen in cross-section through the ring is thinner in the anterior and posterior regions than in the side regions.

23. The mitral annuloplasty ring of claim 20, wherein the core is a round metallic wire.

24. The mitral annuloplasty ring of claim 20, wherein the core is a formed metal ring having a concave outer surface.

25. The mitral annuloplasty ring of claim 20, wherein the core is metal ring and has an axially-oriented outer surface.

26. A mitral annuloplasty ring, comprising:
    a semi-flexible metallic inner core having an anterior region and a posterior region opposite the anterior region, and two side regions between the anterior and posterior regions, and wherein trigones are defined at the junction between the anterior region and the two side regions, the ring having a vertical dimension extending between the anterior region and posterior region and a larger transverse dimension extending between the side regions, and wherein the radial width of the core has a maximum at the side regions that is greater than both the anterior and posterior regions;

an outer band located around the outside of the inner core for anchoring the ring to a mitral annulus; and wherein there is a gradual reduction in cross-section in the radial width of the core between the side regions and at least one of the anterior and posterior regions.

27. The mitral annuloplasty ring of claim 26, wherein the radial width of the core is thinner in both the anterior and posterior regions than in the side regions.

28. The mitral annuloplasty ring of claim 26, wherein the difference in width dimension of the core in the anterior and posterior regions relative to the side regions is such that the core is 20% more rigid in the vertical dimension as compared to the transverse dimension.

29. The mitral annuloplasty ring of claim 26, wherein the core is a round metallic wire.

30. The mitral annuloplasty ring of claim 26, wherein the core is a formed metal ring having a concave outer surface.

31. The mitral annuloplasty ring of claim 26, wherein the core is metal ring and has an axially-oriented outer surface.

32. A mitral annuloplasty ring, comprising:

a semi-flexible metallic inner core having an anterior region and a posterior region opposite the anterior region, and two side regions between the anterior and posterior regions, and wherein trigones are defined at the junction between the anterior region and the two side regions, the ring having a vertical dimension extending between the anterior region and posterior region and a larger transverse dimension extending between the side regions, and wherein the radial width of the core has a maximum at the side regions that is greater than both the anterior and posterior regions;

an outer band located around the outside of the inner core for anchoring the ring to a mitral annulus; and wherein the radial width of the core at the anterior region is not equal to the radial width of the core at the posterior region.

33. The mitral annuloplasty ring of claim 32, wherein a width dimension of the outer band as seen in cross-section through the ring is greater in the posterior region of the ring than in the anterior region.

34. The mitral annuloplasty ring of claim 32, wherein the anterior and posterior regions rise to different heights.

35. The mitral annuloplasty ring of claim 32, wherein the core is a round metallic wire.

36. The mitral annuloplasty ring of claim 32, wherein the core is a formed metal ring having a concave outer surface.

37. The mitral annuloplasty ring of claim 32, wherein the core is metal ring and has an axially-oriented outer surface.

* * * * *